United States Patent [19]

Cakara et al.

[11] Patent Number: 5,387,703
[45] Date of Patent: Feb. 7, 1995

[54] PROCESS AND INTERMEDIATE FOR THE PURIFICATION OF OXYTETRACYCLINE

[75] Inventors: Marija Cakara, Marulicev trg; Bozidar Suskovic, Tuskanec, both of

[73] Assignee: Pliva, Zagreb,

[21] Appl. No.: 138,221

[22] Filed: Oct. 20, 1993

[51] Int. Cl.$^6$ .................. C07C 233/88; C07C 235/42
[52] U.S. Cl. ...................... 552/203; 552/206
[58] Field of Search .................. 552/203, 206

[56] References Cited

U.S. PATENT DOCUMENTS

| | | | |
|---|---|---|---|
| 2,649,480 | 8/1953 | Regna et al. | 260/559 |
| 2,658,078 | 11/1953 | Blase | 260/559 |
| 2,763,682 | 9/1956 | Winterbottom et al. | 260/559 |
| 2,873,276 | 2/1959 | Blase | 260/295 |
| 2,886,595 | 5/1959 | Heinemann et al. | 260/559 |
| 2,897,234 | 7/1959 | Heinemann et al. | 260/559 |
| 2,929,837 | 3/1960 | Ogawa et al. | 260/501 |
| 2,992,274 | 7/1961 | Bernardi | 260/559 |
| 3,037,973 | 6/1962 | Sarcona et al. | 260/96.5 |
| 3,349,127 | 10/1967 | Culik et al. | 260/559 |
| 3,397,231 | 8/1968 | Korst | 260/559 |
| 3,454,639 | 7/1969 | Putnam | 260/559 |
| 4,579,686 | 4/1986 | Szarvas et al. | 260/351.6 |
| 4,581,166 | 4/1986 | Peter et al. | 260/112.5 |

Primary Examiner—Howard T. Mars
Assistant Examiner—Kimberly J. Kestler
Attorney, Agent, or Firm—Pollock, Vande Sande & Priddy

[57] ABSTRACT

The invention relates to a new process for obtaining a completely pure oxytetracycline which does not contain any acetyldecarboxamidoöxytetracycline as ingredient. In glacial acetic acid there is suspended under stirring oxytetracycline hydrochloride, or alternatively, oxytetracycline dihydrate under addition of an equimolar quantity of hydrogen chloride in the form of concentrated hydrochloric acid. The stirring is continued for 5 hours, the formed oxytetracycline hydrochloride acetate precipitate is filtered, washed with glacial acetic acid and acetone, whereupon it is dried under reduced pressure at a temperature up to 40° C. till constant weight. Oxytetracycline hydrochloride acetate

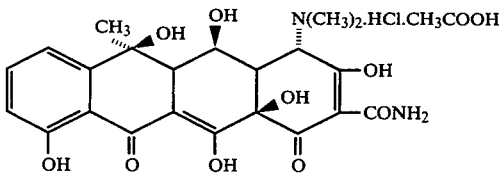

is a new compound and may be used as intermediate in the above process.

2 Claims, No Drawings

PROCESS AND INTERMEDIATE FOR THE PURIFICATION OF OXYTETRACYCLINE

The present invention relates to a new process for obtaining a completely pure oxytetracycline with no acetyldecarboxamidoöxytetracycline content, as well as to a new intermediate for the performance thereof.

It has been known, that tile fermentation of oxytetracycline of the following formula (I) yields as by-product also 3-12.5% of 2-acetyl-2-decarboxamidoöxytetracycline (in the following text acetyldecarboxamidoöxytetracycline) of the following formula II

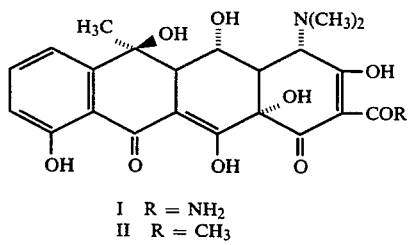

I  R = NH₂
II R = CH₃

By using standard methods of isolation of oxytetracycline from the fermentation broth and the further purification thereof its content of acetyldecarboxamidoöxytetracycline is only slightly reduced and is left as an impurity in the final product oxytetracycline. The presence of acetyldecarboxamidoöxytetracycline as a byproduct in oxytetracycline was demonstrated for the first time by chromatographic separation of these two compounds on a thin layer (Archiv der Pharmazie 300, 840/1967/). There were tested 15 samples of oxytetracycline of various producers of this antibiotic and the presence of acetyldecarboxamidoöxytetracycline therein was qualitatively confirmed. Quantitatively, the content of acetyldecarboxamidoöxytetracycline in oxytetracycline samples was defined by means of high pressure liquid chromatography (in the following text HPLC) (Journal of Chromatography 405,229/1987/).

Acetyldecarboxamidoöxytetracycline was obtained by fermentation even earlier. The substance was isolated and purified by counter-current distribution, and chemically identified (Journal of American Chemical Society 82, 5934/1960/), and patented as antibiotic (U.S. Pat. No. 3,022,347 /1962/). The investigation of biological activity of acetyldecarboxamidoöxytetracycline on 33 microorganisms confirmed a similar antibacterial spectrum as in oxytetracycline, whereas, its potency did not reach even 10% of that of oxytetracycline.

Owing to the extreme similarity of the oxytetracycline and acetyldecarboxamidooxytetracycline molecules there has not been hitherto described any process for the isolation of oxytetracycline, which would be completely devoid of acetyldecarboxamidoöxytetracycline.

It has been known as well that oxytetracycline forms molecular salt complexes with various organic acids and bases (JP-Patent No. 17 044 /63/; Chem. Abstr. 60, 2875 a). The crystal structure of some of these salts was determined by X-ray diffraction method (Bull. Chem. Soc. Japan 36, 1163-8 /1963/). Molecular salt complexes of oxytetracycline hydrochloride with oxalic acid, pirazine and monochloroacetic acid have been described.

It has been now surprisingly found that oxytetracycline hydrochloride, dissolved in glacial acetic acid forms a molecular salt complex, namely oxytetracycline hydrochloride acetate. A remarkable solubility difference of the molecular salt complexes of oxytetracycline and of acetyldecarboxamidoöxytetracycline in glacial acetic acid enables an efficient separation of one from the other. Namely, if oxytetracycline hydrochloride containing acetyldecarboxamidoöxytetracycline hydrochloride (about 3%) as an impurity is suspended in glacial acetic acid, the salt is at first completely dissolved, whereupon oxytetracycline is precipitated in the form of a molecular salt complex. The molecular salt complex of acetyldecarboxamidoöxytetracycline is at these conditions highly soluble and remains substantially in the solution. Upon filtration of the precipitated oxytetracycline hydrochloride acetate there is isolated in an excellent yield oxytetracycline with a content of acetyldecarboxamidoöxytetracycline reduced to 0.3-0.5%, as confirmed by HPLC method. The filtrate comprises practically all the present acetyldecarboxamidoöxytetracycline and about 1-2% of the initial quantity of oxytetracycline, which may be regenerated by evaporation of the filtrate. Oxytetracycline may be subjected to such a purification also in the form of its base (dihydrate, in the following text oxytetracycline dihydrate). In this case also an equimolar quantity of hydrogen chloride is added in the form of concentrated hydrochloric acid to the solution of oxytetracycline dihydrate in glacial acetic acid, which enables the formation of the molecular salt complex oxytetracycline hydrochloride acetate. After the precipitation of the complex has started toluene may be added in a quantity of up to 80 vol. % of the present glacial acetic acid, with the aim to reduce the solubility of the product. If the crude oxytetracycline dihydrate is chosen as starting material, it should be preferably previously converted—using well known standard procedures—into oxytetracycline hydrochloride, which may be subsequently without drying further converted into oxytetracycline hydrochloride acetate. The ratio of glacial acetic acid in relation to oxytetracycline may be within 1.5-5 mL/mmole of oxytetracycline, whereas, the best result was attained with a ratio of 2.5 mL/mmole of oxytetracycline.

The process of tile present invention is performed in such a manner, that in glacial acetic acid there is suspended under stirring oxytetracycline hydrochloride, or alternatively, oxytetracycline dihydrate under addition of an equimolar quantity of hydrogen chloride in the form of concentrated hydrochloric acid. The stirring is kept on for further 5 hours. During the first hour of stirring oxytetracycline is completely dissolved, after which the molecular salt complex is precipitated. Upon 5 hours of stirring the precipitate is filtered, washed with glacial acetic acid and acetone, whereupon it is dried under reduced pressure at a temperature of up to 40° C. till constant weight. The yields of the isolated oxytetracycline hydrochloride acetate vary in dependence of the purity of the starting material. The yields are higher, if the starting material is purer. Oxytctracycline hydrochloride acetate is a well-crystalized and stable, yellow coloured salt which may be without major losses converted into oxytetracycline hydrochloride or oxytetracycline dihydrate. The conversion into oxytetracycline hydrochloride is performed by dissolving oxytetracycline hydrochloride acetate in a minimal quantity of water and the addition of a mixture of methanol and concentrated hydrochloric acid. By repeating the complete process, starting from such purified oxytetracycline hydrochloride the completely pure oxytetracycline hydrochloride acetate with no acetyldecarboxamidoöxytetracycline content is obtained. The conversion of oxytetracycline hydrochloride acetate into oxytetracycline dihydrate is performed by dissolving oxytetracycline hydrochloride acetate in water, in such a quantity, that the concentration of oxytetracycline in the solution is about 50,000 IU/mL, and the adjustment of the pH of the solution to 5, resulting in the precipitation of oxytetracycline dihydrate, which is finally isolated by filtration.

Oxytetracycline hydrochloride acetate, which is isolated from the solution of oxytetracycline in glacial acetic acid is a molecular salt complex, which has not been described as yet. Its molecular composition was established by titration with sodium hydroxide and silver nitrate and by determination of the acetic acid content by gas chromatography. The salt complex was found to consist of each oxytetracycline, hydrogen chloride, and acetic acid in equimolar ratio, thus corresponding to the formula III:

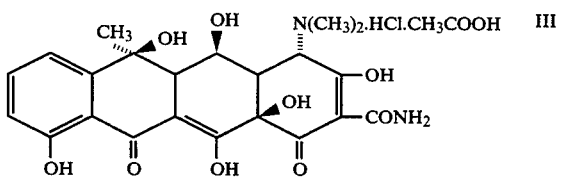

The molecule of this composition contains theoretically 6.55% of hydrogen chloride and 10.78% of acetic acid, whereas, the biological activity calculated on dry matter, is 826.7 IU/mg. The values, which were obtained by the analysis of the prepared oxytetracycline hydrochloride acetate samples, differ from the theoretical ones within the limits of a few percents. Thus, there was in various samples determined a hydrogen chloride content of 6.2–6.7%, the acetic acid content of 10.2–11.5%, and the biological potency of 800–836 IU/mg. Like all tetracycline compounds, oxytetracycline hydrochloride acetate has no sharp melting point. Upon heating the substance changes its colour at a temperature exceeding 170° C., whereas, it is totally decomposed at a temperature exceeding 200° C.

The presence of acetic acid in the molecule is evidenced by the spectral characteristics of the new compound. Thus, the UV spectrum is according to the maxima distribution identical to the spectrum of oxytetracycline hydrochloride, except that the absorbances are diminished owing to the increase of the molecular mass. For the same reason the value of specific optical rotation is also lower. In $^1$H and $^{13}$C NMR spectra oxytetracycline hydrochloride acetate shows all signals of oxytetracycline at their usual sites, in addition to signals for acetic acid. Upon mass spectrography of oxytetracycline hydrochloride acetate there were obtained in addition of fragments, characteristic for oxytetracycline, also mass fragments of 43 and 60, deriving from acetic acid.

Because of the extremely low biological activity of acetyldecarboxamidoöxytetracycline its presence in oxytetracycline is an inactive ballast. By removing this ballast its useless precipitation in the bones of the human organism is avoided, whereas, oxytetracycline of an improved microbiological potency is obtained. This means, that upon medical administration the same effect is achieved with a lower dose of the medicament.

The present invention is illustrated, but in no manner limited, by the following Examples.

EXAMPLE 1

Preparation of oxytetracycline hydrochloride acetate from oxytetracycline hydrochloride Oxytetracycline hydrochloride (100 g; 890 IU/mg; the content determined by HPLC method: 91.9% oxytetracycline and 2.6% acetyldecarboxamidoöxytetracycline, expressed as hydrochlorides) was suspended in 500 mL of glacial acetic acid and the suspension was stirred for 5 hours at room temperature. After about 1 hour a clear solution was obtained, whereupon a yellow precipitate was beginning to form. Upon 5 hours of stirring the precipitate was filtered, washed with 50 mL of cooled glacial acetic acid and 50 mL of acetone, and dried under reduced pressure till constant weight. Yield: 110 g (98%).

Determination by means of HPLC method; the product comprises oxytetracycline and acetyldecarboxamidoöxytetracycline in a ratio of 99.6:0.4.

Bioassay: 829 IU/mg. Acetic acid content: 10.23%. Water (K. Fisher method): 1.0%. HCl (titration with AgNO$_3$): 6.6%. M.p.=203°–208° C. (decomposition). $[\alpha]_d^{20}$: −172.1 UV$\lambda_{max}$: 218 nm (A$^{1\%}$ 248.41), 268 nm (A$^{1\%}$ 336.63) and 360 nm (A$^{1\%}$ 251.87) (0.01 N HCl/EtOH).

EXAMPLE 2

Preparation of oxytetracycline hydrochloride acetate from the crude oxytetracycline dihydrate via the oxytetracycline hydrochloride The crude oxytetracycline dihydrate (content by HPLC: 95.6% oxytetracycline dihydrate and 3.0% acetyldecarboxamidoöxytetracycline dihydrate) was converted by means of a standard procedure into oxytetracycline hydrochloride: the crude dihydrate (100 g) was under stirring and heating on a water bath to 30° C. dissolved in a mixture of 750 mL of methanol and 12 mL of concentrated hydrochloric acid. Upon working up with 0.5 g of disodium salt of ethylenediaminotetraacetic acid and 1.5 g of active carbon the suspension was filtered under addition of 1.5 g of filtration earth and the filter cake was washed with 100 mL of methanol. Oxytetracycline hydrochloride was precipitated in the filtrate by slow addition, while stirring and cooling, of 55 mL of concentrated hydrochloric acid. After the filtration and drying in an air circulation drying oven at 50° C. there was obtained 97.06 g of oxytetracycline hydrochloride. The complete product was under stirring dissolved in 500 mL of glacial acetic acid. After 10 minutes the obtained clear solution was seeded with 0.1 g of oxytetracycline hydrochloride acetate, and was stirred for 5 hours at room temperature. Following the identical procedure, as in Example 1, there was obtained 98.5 g of oxytetracycline hydrochloride acetate. The content of the product, as determined by HPLC, was 99.07% oxytetracycline hydrochloride acetate and 0.56% acetyldecarboxamidoöxytetracycline hydrochloride acetate. Yield of regenerated oxytetracycline: 90.98%.

EXAMPLE 3

Preparation of oxytetracycline hydrochloride acetate directly from the crude oxytetracycline dihydrate The crude oxytetracycline dihydrate (200 g; 913 IU/mg; water: 6.9%; content by HPLC: 98.5% oxytetracycline dihydrate and 2.1% acetyldecarboxamidoöxytetracycline dihydrate) was suspended in 600 mL of glacial acetic acid, and 32 mL of concentrated hydrochloric acid was added dropwise under stirring to the suspension. Upon stirring a solution was obtained, which was seeded with 0.1 g of oxytetracycline hydrochloride acetate. Upon stirring for 1.5 hours there was added 400 mL of toluene and the stirring was continued. After totally 5 hours of stirring the obtained precipitate was filtered, the filter cake was stirred with 400 mL of acetone, once more filtered and washed with additional 400 mL of acetone. The product was dried at room temperature and reduced pressure. There was obtained 188.06 g of oxytetracycline hydrochloride acetate, comprising (by HPLC method): 98.5 % oxytetracycline hydrochloride acetate and 0.45% acetyldecarboxamidoöxytetracycline hydrochloride acetate. Yield of regenerated oxytetracycline: 83.8%.

EXAMPLE 4

Preparation of oxytetracycline dihydrate from oxytetracycline hydrochloride acetate The oxytetracycline hydrochloride acetate (9.85 g), as obtained in Example 2 was dissolved in 155 mL of distilled water. Concentrated ammonia was dropwise added under stirring to the acidic solution (pH=2.3), and oxytetracycline dihydrate precipitated. After the pH of the mixture reached 5, the stirring was continued for 1 hour, the precipitate was filtered, washed with 50 mL of water and dried under reduced pressure at 40°–50° C. There was obtained 8.6 g of oxytetracycline dihydrate of a biological activity: 921 IU/mg (water: 7.1%; 991 IU/mg calculated on the dry substance). The product comprised (by HPLC) 98.9% oxytetracycline dihydrate and 0.4% acetyldecarboxamidoöxytetracycline dihydrate. The yield of the regenerated oxytetracycline was 87.16%.

EXAMPLE 5

Preparation of oxytetracycline hydrochloride from oxytetracycline hydrochloride acetate The oxytetracycline hydrochloride acetate (95.7 g), as obtained in Example 2, was dissolved under stirring in 100 mL of distilled water. To the solution was added dropwise under stirring a mixture of 660 mL of methanol and 110 mL of concentrated hydrochloric acid. The addition was performed at room temperature till oxytetracycline hydrochloride began to crystalise (about ⅓ of the mixture), whereas, the residual mixture was added dropwise under cooling at about +2° C. After all the mixture was added, the precipitated crystals were allowed to stand under cooling without agitation for 1 additional hour, filtered, washed with 100 mL of cooled methanol and dried under reduced pressure at 40° C. There was obtained 80.64 g of oxytetracycline hydrochloride of a biological potency: 918 IU/mg (water: 0.6%; 924 IU/mg calculated on dry matter). The product comprised (by HPLC) 93.9% oxytetracycline hydrochloride and 0.5% acetyldecarboxamidoöxytetracycline hydrochloride. The yield of the regenerated oxytetracycline was 89.6%.

In the same manner there was worked up the oxytetracycline hydrochloride acetate, as obtained in Example 3. The product of Example 3 (188.06 g) was dissolved in 185 mL of water. The minor quantity of undissolved impurities was filtered through a layer of filtration earth and the filter cake was washed with a mixture of 10 mL of methanol and 1 mL of water. Upon dropwise addition of a mixture of 1050 mL of methanol and 192 mL of concentrated hydrochloric acid, under the conditions described for the working up of the product of Example 2, there was precipitated oxytetracycline hydrochloride from the filtrate. Upon filtration and drying there was obtained 134.3 g of oxytetracycline hydrochloride of a biological potency: 933 IU/mg and comprising (by HPLC) 97.2% oxytetracycline hydrochloride and 0.4% acetyldecarboxamidoöxytetracycline hydrochloride.

The yield of the regenerated oxytetracycline: 79.07%.

EXAMPLE 6

Preparation of the pure oxytetracycline hydrochloride

The oxytetracycline hydrochloride (50 g), as obtained in Example 5, was converted according to the process, described in Example 1, into the oxytetracycline hydrochloride acetate. The obtained oxytetracycline hydrochloride acetate (49 g) was then converted into oxytetracycline hydrochloride according to the process, as described in Example 5. There was obtained 39.36 g of oxytetracycline hydrochloride of biological potency: 924 IU/mg (water 0.6%) and comprising (by HPLC): 97.7% oxytetracycline hydrochloride and 0% acetyldecarboxamidoöxytetracycline hydrochloride.

We claim:

1. A process for the preparation of pure oxytetracycline, characterized in that oxytetracycline hydrochloride or alternatively, oxytetracycline dihydrate and an equimolar quantity of hydrogen chloride in the form of concentrated hydrochloric acid is suspended in glacial acetic acid under stirring, the stirring is continued for 5 hours, the formed oxytetracycline hydrochloride acetate precipitate is filtered, washed with glacial acetic acid and acetone, and dried under reduced pressure at a temperature up to 40° C. till constant weight.

2. Oxytetracycline hydrochloride acetate of the formula

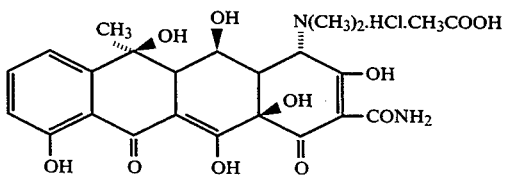

* * * * *